US 7,468,420 B2

United States Patent
Schmidt, Jr. et al.

(10) Patent No.: US 7,468,420 B2
(45) Date of Patent: *Dec. 23, 2008

(54) PROCESS FOR PURIFYING GLYCOPEPTIDE PHOSPHONATE DERIVATIVES

(75) Inventors: Donald E. Schmidt, Jr., Brisbane, CA (US); Jeanmarie Donovan Sganga, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/977,605

(22) Filed: Oct. 25, 2007

(65) Prior Publication Data

US 2008/0103290 A1 May 1, 2008

Related U.S. Application Data

(63) Continuation of application No. 11/301,740, filed on Dec. 13, 2005, which is a continuation of application No. 10/226,676, filed on Aug. 23, 2002, now Pat. No. 7,015,307.

(60) Provisional application No. 60/314,712, filed on Aug. 24, 2001.

(51) Int. Cl.
*C07K 14/00* (2006.01)

(52) U.S. Cl. ...................................... 530/322; 514/110

(58) Field of Classification Search ...................... None
See application file for complete search history.

(56) References Cited

U.S. PATENT DOCUMENTS

| 4,440,753 | A | 4/1984 | McCormick et al. |
| 4,667,024 | A | 5/1987 | Sitrin et al. |
| 4,845,194 | A | 7/1989 | Glass et al. |
| 4,874,843 | A | 10/1989 | Baker |
| 4,994,555 | A | 2/1991 | Panzone et al. |
| 5,149,784 | A | 9/1992 | Chu |
| 5,258,495 | A | 11/1993 | Chu |
| 5,853,720 | A | 12/1998 | Pflaum et al. |
| 6,635,618 | B2 | 10/2003 | Leadbetter et al. |
| 7,015,307 | B2 * | 3/2006 | Schmidt et al. ............. 530/330 |
| 2002/0022590 | A1 | 2/2002 | Leadbetter et al. |
| 2006/0100415 | A1 * | 5/2006 | Schmidt et al. ............. 530/322 |

FOREIGN PATENT DOCUMENTS

| EP | 0 299 707 A2 | 1/1989 |
| WO | WO 91/08300 | 6/1991 |
| WO | WO 93/21207 | 10/1993 |
| WO | WO 98/26085 | 6/1998 |
| WO | WO 01/98328 A2 | 12/2001 |

* cited by examiner

*Primary Examiner*—Christopher R. Tate
*Assistant Examiner*—Roy Teller
(74) *Attorney, Agent, or Firm*—Jeffrey A. Hagenah

(57) ABSTRACT

Disclosed are methods of purifying glycopeptides that are substituted with one or more substituents each comprising one or more phosphono groups that are useful as antibacterial agents. The methods include contacting a solution of the glycopeptide derivatives with a polystyrene-containing resin, eluting the resin with an aqueous solution, and isolating the purified glycopeptide derivative.

7 Claims, No Drawings

PROCESS FOR PURIFYING GLYCOPEPTIDE PHOSPHONATE DERIVATIVES

CROSS-REFERENCE TO RELATED APPLICATIONS

This application is continuation of U.S. application Ser. No. 11/301,740, filed Dec. 13, 2005, which application is a continuation of U.S. application Ser. No. 10/226,676, filed Aug. 23, 2002 (now U.S. Pat. No. 7,015,307); which application claims the benefit of U.S. Provisional Application No. 60/314,712, filed on Aug. 24, 2001; the entire disclosures of which are incorporated herein by reference in their entirety.

BACKGROUND OF THE INVENTION

1. Field of the Invention

This invention is directed to purification of novel phosphonate derivatives of glycopeptide antibiotics and related compounds. In particular, this invention is directed to purification of glycopeptide phosphonate derivatives by resin chromatography methods.

2. Background

Glycopeptides (e.g. dalbaheptides) are a well-known class of antibiotics produced by various microorganisms (see *Glycopeptide Antibiotics*, edited by R. Nagarajan, Marcel Dekker, Inc. New York (1994)). These complex multi-ring peptide compounds are very effective antibacterial agents against a majority of Gram-positive bacteria. Although potent antibacterial agents, the glycopeptides antibiotics are not used in the treatment of bacterial diseases as often as other classes of antibiotics, such as the semi-synthetic penicillins, cephalosporins and lincomycins, due to concerns regarding toxicity.

In recent years, however, bacterial resistance to many of the commonly-used antibiotics has developed (see J. E. Geraci et al., *Mayo Clin. Proc.* 1983, 58, 88-91; and M. Foldes, *J. Antimicrob. Chemother.* 1983, 11, 21-26). Since glycopeptide antibiotics are often effective against these resistant strains of bacteria, glycopeptides such as vancomycin have become the drugs of last resort for treating infections caused by these organisms. Recently, however, resistance to vancomycin has appeared in various microorganisms, such as vancomycin-resistant enterococci (VRE), leading to increasing concerns about the ability to effectively treat bacterial infections in the future (see Hospital Infection Control Practices Advisory Committee, *Infection Control Hospital Epidemiology*, 1995, 17, 364-369; A. P. Johnson et al., Clinical Microbiology Rev., 1990, 3, 280-291; G. M. Eliopoulos, *European J. Clinical Microbiol., Infection Disease*, 1993, 12, 409-412; and P. Courvalin, *Antimicrob. Agents Chemother*, 1990, 34, 2291-2296).

A number of derivatives of vancomycin and other glycopeptides are known in the art. For example, see U.S. Pat. Nos. 4,639,433; 4,643,987; 4,497,802; 4,698,327; 5,591,714; 5,840,684; and 5,843,889. Other derivatives are disclosed in EP 0 802 199; EP 0 801 075; EP 0 667 353; WO 97/28812; WO 97/38702; WO 98/52589; WO 98/52592; and in *J. Amer. Chem. Soc.*, 1996, 118, 13107-13108; *J. Amer. Chem. Soc.*, 1997, 119, 12041-12047; and *J. Amer. Chem. Soc.*, 1994, 116, 45734590.

The preparation of glycopeptide antibiotics generally includes a purification step. Methods suitable for purifying gylcopeptides, particularly vancomycin and related compounds, are described, for example in U.S. Pat. Nos. 4,440, 753, 4,845,194, 4,874,843, 5,149,784, 5,258,495, and 5,853, 720. Other methods are disclosed in WO 91/08300 and WO 93/21207.

Despite the above referenced disclosures, a need currently exists for novel glycopeptide derivatives having effective antibacterial activity and an improved mammalian safety profile. In particular, a need exists for glycopeptide derivatives which are effective against a wide spectrum of pathogenic microorganisms, including vancomycin-resistant microorganisms, and which have reduced tissue accumulation and/or nephrotoxicity. Further, in order for these novel derivatives to be useful, there is a need for effective methods of purifying said compounds which recover the product in a highly pure form suitable for pharmaceutical product synthesis.

SUMMARY OF THE INVENTION

The present invention provides methods of purifying novel glycopeptide phosphonate derivatives having highly effective antibacterial activity and an improved mammalian safety profile. More specifically, the present invention provides methods of purifying glycopeptide derivatives by resin chromatography.

The glycopeptide phosphonate derivatives purified according to the methods of the present invention exhibit reduced tissue accumulation and/or nephrotoxicity when administered to a mammal. The glycopeptide compounds are substituted with one or more (e.g., 1, 2 or 3) substituents comprising one or more (e.g., 1, 2 or 3) phosphono ($-PO_3H_2$) groups; or a pharmaceutically acceptable salt, stereoisomer, or prodrug thereof. Preferably, the glycopeptide compound is substituted with one or two substituents comprising one or two phosphono groups. More preferably, the glycopeptide compound is substituted with one substituent comprising one or two phosphono groups, preferably one phosphono group. Optionally, the glycopeptide compounds may also be substituted with other substituents not comprising a phosphono group, provided that at least one substituent comprises one or more phosphono groups.

Accordingly, in one preferred derivative a glycopeptide compound is substituted at the C-terminus with a substituent comprising one or two phosphono ($-PO_3H_2$) groups; or a pharmaceutically acceptable salt, stereoisomer, or prodrug thereof. Preferably, the phosphono-containing substituent is attached to the carbonyl group at the C-terminus through an amide bond, an ester bond, or a thioester bond; more preferably, through an amide bond. Preferably, the phosphono-containing substituent comprises one phosphono group. Particularly preferred phosphono-containing substituents at the C-terminus include phosphonomethylamino, 3-phosphonopropylamino and 2-hydroxy-2-phosphonoethylamino.

In another preferred derivative, a glycopeptide compound is substituted at the R-terminus (on the resorcinol ring) with a substituent comprising one or two phosphono ($-PO_3H_2$) groups; or a pharmaceutically acceptable salt, stereoisomer, or prodrug thereof. Preferably, the phosphono-containing substituent is attached to the R-terminus (i.e., the resorcinol ring) through the nitrogen atom of an aminomethyl group attached to the R-terminus. Preferably, the phosphono-containing substituent comprises one phosphono group. Particularly preferred phosphono-containing substituents at the R-terminus include N-(phosphonomethyl)aminomethyl; -(2-hydroxy-2-phosphonoethyl)aminomethyl; N-carboxymethyl-N-(phosphonomethyl)aminomethyl; N,N-bis(phosphonomethyl)aminomethyl; and N-(3-phosphonopropyl)aminomethyl.

In still another preferred derivative, a glycopeptide compound is substituted at the C-terminus and at the R-terminus with a substituent comprising one or two phosphono (—PO$_3$H$_2$) groups; or a pharmaceutically acceptable salt, stereoisomer, or prodrug thereof. Preferably, the phosphono-containing substituents each comprises one phosphono group.

A preferred glycopeptide derivative is a glycopeptide of formula I:

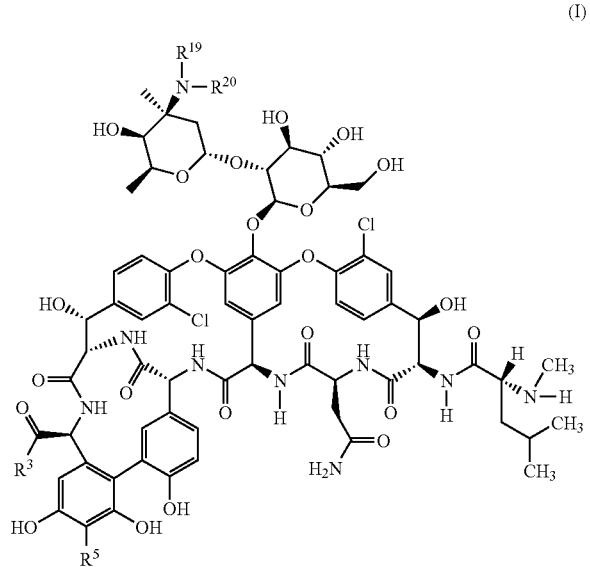

(I)

wherein:
R$^{19}$ is hydrogen;
R$^{20}$ is —R$^a$—Y—R$^b$-(Z)$_x$, R$^f$, —C(O) R$^f$, or —C(O)—R$^a$—Y—R$^b$-(Z)$_x$;
R$^3$ is —OR$^c$, —NR$^c$R$^c$, —O—R$^a$—Y—R$^b$-(Z)$_x$, —NR$^c$—R$^a$—Y—R$^b$-(Z)$_x$, —NR$^c$R$^e$ or —O—R$^e$; or R$^3$ is a nitrogen-linked, oxygen-linked, or sulfur-linked substituent that comprises one or more phosphono groups;
R$^5$ is selected from the group consisting of hydrogen, halo, —CH(R$^c$)—NR$^c$R$^c$, —CH(R$^c$)—NR$^c$R$^e$, —CH(R$^c$)—NR$^c$—R$^a$—Y—R$^b$-(Z)$_x$, —CH(R$^c$)—R$^x$, —CH(R$^c$)—NR$^c$—R$^a$—C(=O)—R$^x$, and a substituent that comprises one or more phosphono groups;
each R$^a$ is independently selected from the group consisting of alkylene, substituted alkylene, alkenylene, substituted alkenylene, alkynylene and substituted alkynylene;
each R$^b$ is independently selected from the group consisting of a covalent bond, alkylene, substituted alkylene, alkenylene, substituted alkenylene, alkynylene and substituted alkynylene, provided R$^b$ is not a covalent bond when Z is hydrogen;
each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;
each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;
R$^e$ is a saccharide group;
each R$^f$ is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;
R$^x$ is an N-linked amino saccharide or an N-linked heterocycle;
each Y is independently selected from the group consisting of oxygen, sulfur, —S—S—, —NR$^c$—, —S(O)—, —SO$_2$—, —NR$^c$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(=O)—, and —NR$^c$SO$_2$NR$^c$—;
each Z is independently selected from hydrogen, aryl, cycloalkyl, cycloalkenyl, heteroaryl and heterocyclic; and
x is 1 or 2;
or a pharmaceutically acceptable salt, stereoisomer, or prodrug thereof;
provided at least one of R$^3$ and R$^5$ is a substituent comprising one or more phosphono groups.
Preferably, R$^{20}$ is —CH$_2$CH$_2$—NH—(CH$_2$)$_9$CH$_3$; —CH$_2$CH$_2$CH$_2$—NH—(CH$_2$)$_8$CH$_3$; —CH$_2$CH$_2$CH$_2$CH$_2$—NH—(CH$_2$)$_7$CH$_3$; —CH$_2$CH$_2$—NHSO$_2$—(CH$_2$)$_9$CH$_3$; —CH$_2$CH$_2$—NHSO$_2$—(CH$_2$)$_{11}$CH$_3$; —CH$_2$CH$_2$—S—(CH$_2$)$_8$CH$_3$; —CH$_2$CH$_2$—S—(CH$_2$)$_9$CH$_3$; —CH$_2$CH$_2$—S—(CH$_2$)$_{10}$CH$_3$; —CH$_2$CH$_2$CH$_2$—S—(CH$_2$)$_8$CH$_3$; —CH$_2$CH$_2$CH$_2$—S—(CH$_2$)$_9$CH$_3$; —CH$_2$CH$_2$CH$_2$—S—(CH$_2$)$_3$—CH=CH—(CH$_2$)$_4$CH$_3$ (trans); —CH$_2$CH$_2$CH$_2$CH$_2$—S—(CH$_2$)$_7$CH$_3$; —CH$_2$CH$_2$—S(O)—(CH$_2$)$_9$CH$_3$; —CH$_2$CH$_2$—S—(CH$_2$)$_6$Ph; —CH$_2$CH$_2$—S—(CH$_2$)$_8$Ph; —CH$_2$CH$_2$CH$_2$—S—(CH$_2$)$_8$Ph; —CH$_2$CH$_2$—NH—CH$_2$-4-(4-Cl—Ph)-Ph; —CH$_2$CH$_2$—NH—CH$_2$-4-[4-(CH$_3$)$_2$CHCH$_2$—]-Ph; —CH$_2$CH$_2$—NH—CH$_2$-4-(4-CF$_3$-Ph)-Ph; —CH$_2$CH$_2$—S—CH$_2$-4-(4-Cl-Ph)-Ph; —CH$_2$CH$_2$—S(O)—CH$_2$-4-(4-Cl-Ph)—Ph; —CH$_2$CH$_2$CH$_2$—S—CH$_2$-4-(4-Cl-Ph)-Ph; —CH$_2$CH$_2$CH$_2$—S(O)—CH$_2$-4-(4-Cl-Ph)—Ph; —CH$_2$CH$_2$CH$_2$—S—CH$_2$-4-[3,4-di-Cl-PhCH$_2$O—)-Ph; —CH$_2$CH$_2$—NHSO$_2$—CH$_2$-4-[4-(4-Ph)-Ph]-Ph; —CH$_2$CH$_2$CH$_2$—NHSO$_2$—CH$_2$-4-(4-Cl-Ph)-Ph; —CH$_2$CH$_2$CH$_2$—NHSO$_2$—CH$_2$-4-(Ph-C≡C—)-Ph; —CH$_2$CH$_2$CH$_2$—NHSO$_2$-4-(4-Cl-Ph)—Ph; or —CH$_2$CH$_2$CH$_2$—NHSO$_2$-4-(naphth-2-yl)-Ph. Preferably R$^{20}$ is also a 4-(4-chlorophenyl)benzyl group or a 4-(4-chlorobenzyloxy)benzyl group.

Alternatively, the glycopeptide derivative is a compound of formula I, wherein R$^{19}$ is hydrogen; R$^{20}$ is —CH$_2$CH$_2$NH—(CH$_2$)$_9$CH$_3$; R$^3$ is —OH; and R$^5$ is a substituent comprising a phosphono group; or a pharmaceutically acceptable salt thereof.

In yet another alternative, the glycopeptide derivative is a compound of formula I, wherein R$^{19}$ is hydrogen; R$^{20}$ is —R$^a$—Y—R$^b$-(Z)$_x$, R$^f$, —C(O)R$^f$, or —C(O)—R$^a$—Y—R$^b$-(Z)$_x$; R$^3$ is —OH; and R$^5$ is —CH$_2$—NH—CH$_2$—P(O)(OH)$_2$; or a pharmaceutically acceptable salt thereof.

The compounds described above are highly effective antibacterial agents. The present glycopeptide compounds and methods of treating a mammal having a bacterial disease, comprising administering to the mammal a therapeutically effective amount of a compound of the invention, are further described in commonly assigned U.S. patent application Ser. No. 09/847,042, filed May 1, 2001, the disclosure of which is incorporated herein by reference.

A method for preparing a glycopeptide which is substituted at the C-terminus with a substituent that comprises one or more phosphono groups, comprises coupling a corresponding starting glycopeptide wherein the C-terminus is a carboxy group with a suitable phosphono containing compound.

A method for preparing a glycopeptide which is substituted at the R-terminus with a substituent that comprises one or more phosphono groups, comprises coupling a corresponding starting glycopeptide wherein the R-terminus is unsubstituted with a suitable phosphono containing compound. When the starting glycopeptide is substituted at the vancosamine amino terminus, such a method can further optionally comprise preparing the starting glycopeptide by reductively alkylating a corresponding glycopeptide wherein the vancosamine amino terminus is the corresponding amine.

A method for preparing a glycopeptide that is substituted at the C-terminus, comprises derivatizing a corresponding starting glycopeptide wherein the C-terminus is a carboxy group. A method for preparing a glycopeptide which is substituted at the R-terminus, comprising derivatizing a corresponding starting glycopeptide wherein the R-terminus is unsubstituted (i.e. a hydrogen)

In addition, a method for preparing a compound of formula I, wherein $R^3$ is —OH, $R^5$ is —$CH_2$—NH—$R^a$—P(O)(OH)$_2$, $R^{19}$ is hydrogen and $R^{20}$ is —$R^a$—Y—$R^b$-$(Z)_x$ or —$R^f$, and $R^a$, $R^b$, $R^f$, Y, Z and x are as defined herein, or salt thereof comprises the following steps:

(a) reductively alkylating a compound of formula I, wherein $R^3$ is —OH and $R^5$, $R^{19}$ and $R^{20}$ are hydrogen, or a salt thereof, with an aldehyde of the formula HC(O)—$R^{a'}$—Y—$R^b$-$(Z)_x$ or HC(O)$R^{f'}$ wherein $R^{a'}$ and $R^{f'}$ represent $R^a$ and $R^f$, respectively, minus one —$CH_2$— group, to form a compound of formula I wherein $R^3$ is —OH, $R^5$ and $R^{19}$ are hydrogen and $R^{20}$ is —$R^a$—Y—$R^b$-$(Z)_x$ or —$R^f$, or salt thereof, and (b) reacting the product from step (a) with formaldehyde and $H_2N$—$R^a$—P(O)(OH)$_2$ to form a compound of formula I wherein $R^3$ is —OH, $R^5$ is —$CH_2NH$—$R^a$—P(O)(OH)$_2$, $R^{19}$ is hydrogen and $R^{20}$ is —$R^a$—Y—$R^b$-$(Z)_x$ or —$R^f$, or salt thereof.

Preferred glycopeptide compounds of formula I are shown in Table I below wherein $R^{19}$ is hydrogen.

The phosphono compounds described herein have been found to unexpectedly exhibit reduced tissue accumulation and/or nephrotoxicity when administered to a mammal. While not wishing to be bound by theory, it is believed that the phosphono moiety serves to increase the overall negative charge of the glycopeptide under physiological conditions thereby facilitating excretion from the mammal after administration. The unexpected increase in excretion of the present phosphono compounds may be responsible for the reduced tissue accumulation and/or reduced nephrotoxicity observed for these compounds relative to the corresponding compounds that lack the phosphono functionality.

According to embodiments of the present invention, phosphono derivatives of glycopeptides are purified by resin chromatography using resins based on copolymers of polystyrene and divinyl benzene. A wide variety of useful polystyrene resins are provided commercially, for example by TosoHaas (Montgomery, Pa.), Rohm & Haas (Philadelphia, Pa.), Mitsubishi Chemical Industries Ltd. (Tokyo, Japan); and Dow Chemical Co. (Midland, Mich.).

The resins are typically composed of porous beads with a characteristic size in the range of between about 20 μm and about 800 μm having pores with diameters in the range of between about 50 Å and about 1000 Å.

The purification method of the present invention comprises:

contacting a first acidified aqueous solution comprising a glycopeptide phosphonate derivative and a polar organic solvent, with a polystyrene divinyl benzene resin;

eluting the contacted resin with a second acidified aqueous solution comprising a polar organic solvent to form an eluate; and isolating the purified glycopeptide phosphonate derivative from the eluate.

As used here, the term "polar organic solvent" includes methanol, ethanol, isopropyl alcohol, acetonitrile, acetone, n-propyl alcohol, n-butyl alcohol, isobutyl alcohol, methyl

TABLE I

Preferred Compounds of formula I

| Compound | $R^3$ | $R^5$ | $R^{20}$ |
|---|---|---|---|
| 1 | phosphonomethylamino | H | $CH_3(CH_2)_9NHCH_2CH_2$— |
| 2 | phosphonomethylamino | H | $CH_3(CH_2)_9OCH_2CH_2$— |
| 3 | phosphonomethylamino | H | $CH_3(CH_2)_9SCH_2CH_2$— |
| 4 | phosphonomethylamino | H | $CH_3(CH_2)_{12}$— |
| 5 | phosphonomethylamino | H | 4-(4-chlorophenyl)-benzyl |
| 6 | phosphonomethylamino | H | 2-(4-(4-chlorophenyl)-benzylamino)ethyl |
| 7 | phosphonomethylamino | H | 4-(4'-chlorobiphenyl)-butyl |
| 8 | phosphonomethylamino | H | 5-(4'-chlorobiphenyl)-pentyl |
| 9 | 3-phosphonopropylamino | H | $CH_3(CH_2)_9SCH_2CH_2$— |
| 10 | 2-hydroxy-2-phosphonoethylamino | H | 4-(4-chlorophenyl)-benzyl |
| 11 | OH | (phosphonomethyl)-aminomethyl | $CH_3(CH_2)_9NHCH_2CH_2$— |
| 12 | OH | (phosphonomethyl)-aminomethyl | $CH_3(CH_2)_9SCH_2CH_2$— |
| 13 | OH | (phosphonomethyl)-aminomethyl | $CH_3(CH_2)_9OCH_2CH_2$— |
| 14 | OH | (phosphonomethyl)-aminomethyl | $CH_3(CH_2)_{12}$— |
| 15 | OH | (phosphonomethyl)-aminomethyl | 4-(4-chlorophenyl)benzyl |
| 16 | OH | (phosphonomethyl)-aminomethyl | 2-(4-(4-chlorophenyl)-benzylamino)ethyl |
| 17 | OH | (phosphonomethyl)-aminomethyl | 4-(4'-chlorobiphenyl)butyl |
| 18 | OH | (phosphonomethyl)-aminomethyl | 5-(4'-chlorobiphenyl)pentyl |
| 19 | OH | (phosphonomethyl)-aminomethyl | 3-[4-(4-chlorobenzyloxy)-benzylthio]propyl |
| 20 | OH | N-(2-hydroxy-2-phosphonoethyl)-aminomethyl | $CH_3(CH_2)_9SCH_2CH_2$— |
| 21 | OH | N-(carboxymethyl)-N-2-phosphono-methyl)-aminomethyl | $CH_3(CH_2)_9SCH_2CH_2$— |
| 22 | OH | N,N-bis(phosphonomethyl)aminomethyl | $CH_3(CH_2)_9NHCH_2CH_2$— |
| 23 | OH | 3-phosphonopropyl-aminomethyl | $CH_3(CH_2)_9SCH_2CH_2$— |
| 24 | OH | 3-phosphonopropyl-aminomethyl | 4-(4-chlorophenyl)benzyl |
| 25 | phosphonomethylamino | —$CH_2$—N—(N—$CH_3$-D-glucamine | $CH_3(CH_2)_9NHCH_2CH_2$— |
| 26 | OH | (phosphonomethyl)-aminomethyl | —$(CH_2)_3NH$—$SO_2$-4-(4-chlorophenyl)phenyl | ethyl ketone, tetrahydrofuran, and like solvents, which have appreciable water solubility, or are miscible with water. Preferred polar organic solvents are methanol, ethanol, isopropyl alcohol, and acetonitrile.

Suitable acids for the acidification of the first and second aqueous solutions include acetic acid, trifluoroacetic acid, hydrochloric acid, sulfuric acid, phosphoric acid and like acids. For the present invention, acetic acid and hydrochloric acid are preferred.

The purified product is isolated by methods known in the art, such as lyophilization, or precipitation followed by evaporation and/or filtration. Optionally, the isolation process includes a first concentration step in which the eluate is processed using a resin, preferably a polystyrene divinyl benzene resin, to form a solution with a higher concentration of purified product, from which the product is isolated.

In one purification method, the resin is loaded onto a column and the eluate collected in fractions, which are monitored by thin layer chromatography (TLC) and high pressure liquid chromatography (HPLC) for the presence of the glycopeptide. Fractions containing a product concentration and purity higher than a desired threshold are pooled prior to isolating the product. Using the present method, phosphono glycopeptide samples with purity in excess of 80% have been obtained.

DETAILED DESCRIPTION OF THE INVENTION

This invention relates to purification of novel compounds which are derivatives of glycopeptide antibiotics comprising one or more substituents that comprise one or more phosphono groups. When describing the compounds, the following terms have the following meanings, unless otherwise indicated.

Definitions

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 8 substituents, preferably 1 to 5 substituents, and more preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_3$H, guanido, and —SO$_2$-heteroaryl.

The term "alkylene" refers to a diradical of a branched or unbranched saturated hydrocarbon chain, preferably having from 1 to 40 carbon atoms, preferably 1-10 carbon atoms, more preferably 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures. Additionally, the term substituted alkylene includes alkylene groups in which from 1 to 5 of the alkylene carbon atoms are replaced with oxygen, sulfur or —NR— where R is hydrogen or alkyl. Examples of substituted alkylenes are chloromethylene (—CH(Cl)—), aminoethylene (—CH(NH$_2$)CH2-), 2-carboxypropylene isomers (—CH$_2$CH(CO$_2$H)CH$_2$—), ethoxyethyl (—CH$_2$CH$_2$O—CH$_2$CH$_2$—) and the like.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy to (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. This term is exemplified by groups such as ethenylene (—CH═CH—), the propenylene isomers (e.g., —CH$_2$CH═CH— and —C(CH$_3$)═CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1-6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1-6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, sulfonamide, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

The term "carboxy" refers to —COOH.

The term "C-terminus" as it relates to a glycopeptide is well understood in the art. For example, for a glycopeptide of formula I, the C-terminus is the position substituted by the group R$^3$.

The term "dicarboxy-substituted alkyl" refers to an alkyl group substituted with two carboxy groups. This term includes, by way of example, —CH$_2$(COOH)CH$_2$COOH and —CH$_2$(COOH)CH$_2$CH$_2$COOH.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylalkyl" refers to (heteroaryl)alkyl- where heteroaryl and alkyl are as defined herein. Representative examples include 2-pyridylmethyl and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridinylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, oxo (=O), and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula [—(CH$_2$—)$_a$A-] where a is equal to or greater than 2, and A at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "N-terminus" as it relates to a glycopeptide is well understood in the art. For example, for a glycopeptide of formula II, the N-terminus is the position substituted by the group $R^{19}$ and $R^{20}$.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "phosphono" refers to —PO$_3$H$_2$.

The term "phosphonomethylamino" refers to —NH—CH$_2$—P(O)(OH)$_2$.

The term "phosphonomethylaminomethyl" refers to —CH$_2$—NH—CH$_2$—P(O)(OH)$_2$.

The term "prodrug" is well understood in the art and includes compounds that are converted to pharmaceutically active compounds of the invention in a mammalian system. For example, see Remington's Pharmaceutical Sciences, 1980, vol. 16, Mack Publishing Company, Easton, Pa., 61 and 424.

The term "R-terminus" as it relates to a glycopeptide is well understood in the art. For example, for a glycopeptide of formula I, the R-terminus is the position substituted by the group $R^5$.

The term "saccharide group" refers to an oxidized, reduced or substituted saccharide monoradical covalently attached to the glycopeptide or other compound via any atom of the saccharide moiety, preferably via the aglycone carbon atom. The term includes amino-containing saccharide groups. Representative saccharide include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharide are referenced using conventional three letter nomenclature and the saccharide can be either in their open or preferably in their pyranose form.

The term "amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosanine, ristosamine, N-methyl-D-glucamine and the like.

The term "spiro-attached cycloalkyl group" refers to a cycloalkyl group attached to another ring via one carbon atom common to both rings.

The term "stereoisomer" as it relates to a given compound is well understood in the art, and refers another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, *Morrison and Boyde Organic Chemistry*, 1983, 4th ed., Allyn and Bacon, Inc., Boston, Mass., page 123

The term "sulfonamide" refers to a group of the formula —SO$_2$NRR, where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "thioether derivatives" when used to refer to the glycopeptide compounds of this invention includes thioethers (—S—), sulfoxides (—SO—) and sulfones (—SO$_2$—).

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Glycopeptide" refers to oligopeptide (e.g. heptapeptide) antibiotics (dalbaheptides), characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopepodes are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimycin, Chloroorientiein, Chloropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like. The term "glycopeptide" as used herein is also intended to include the general class of peptides disclosed above on which the sugar moiety is absent, i.e. the aglycone series of glycopeptides. For example, removal of the disaccharide moiety appended to the phenol on vancomycin by mild hydrolysis gives vancomycin aglycone. Also within the scope of the invention are glycopeptides that have been further appended with additional saccharide residues, especially aminoglycosides, in a manner similar to vancosamine.

"Optional" or "optionally" means that the subsequently described event or circumstance may or may not occur, and that the description includes instances where said event or circumstance occurs and instances in which it does not. For example, "optionally substituted" means that a group may or may not be substituted with the described substitutent.

As used herein, the terms "inert organic solvent" or "inert solvent" or "inert diluent" mean a solvent or diluent which is essentially inert under the conditions of the reaction in which it is employed as a solvent or diluent. Representative examples of materials which may be used as inert solvents or diluents include, by way of illustration, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "nitrogen-linked" or "N-linked" means a group or substituent is attached to the remainder of a compound (e.g. a compound of formula I) through a bond to a nitrogen of the group or substituent. The term "oxygen-linked" means a group or substituent is attached to the remainder of a compound (e.g. a compound of formula I) through a bond to an oxygen of the group or substituent. The term "sulfur-linked" means a group or substituent is attached to the remainder of a compound (e.g. a compound of formula I) through a bond to a sulfur of the group or substituent.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds described herein typically contain one or more chiral centers. Accordingly, the novel glycopeptide compounds are intended to include racemic mixtures, diasteromers, enantiomers and mixture enriched in one or more stereoisomer.

The term "protecting group" or "blocking group" refers to any group which, when bound to one or more hydroxyl, thiol, amino, carboxy or other groups of the compounds, prevents undesired reactions from occurring at these groups and which protecting group can be removed by conventional chemical or enzymatic steps to reestablish the hydroxyl, thio, amino, carboxy or other group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 3$^{rd}$ Ed., 1999, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxy protecting groups include esters such as methyl, ethyl, propyl, t-butyl etc. which can be removed by mild conditions compatible with the nature of the product.

"Vancomycin" refers to a glycopeptide antibiotic having the formula:

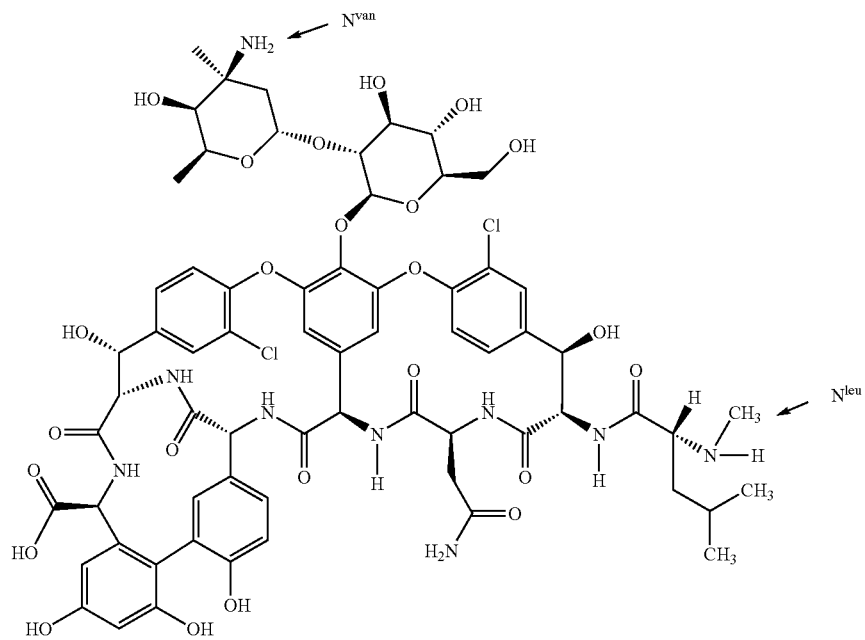

When describing vancomycin derivatives, the term "$N^{van}$-" indicates that a substituent is covalently attached to the amino group of the vacosamine moiety of vacomycin. Similarly, the term "$N^{leu}$-" indicates that a substituent is covalently attached to the amino group of the leucine moiety of vancomycin.

General Synthetic Procedures

The glycopeptide compounds can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In the following reaction schemes, the glycopeptide compounds are depicted in a simplified form as a box "G" that shows the carboxy terminus labeled [C], the vancosamine amino terminus labeled [V], the "non-saccharide" amino terminus (leucine amine moiety) labeled [N], and optionally, the resorcinol moiety labeled [R] as follows:

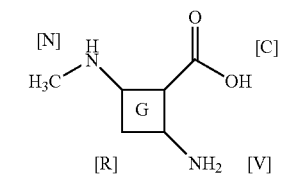

A glycopeptide compound which is substituted at the C-terminus with a substituent that comprises one or more (e.g. 1, 2, 3, 4, or 5) phosphono (—$PO_3H_2$) groups, can be prepared by coupling a corresponding glycopeptide compound wherein the C-terminus is a carboxy group with a suitable phosphono containing compound. For example, a glycopeptide compound wherein the C-terminus is a carboxy group can be coupled with a phosphono containing amine, alcohol, or thiol compound to form an amide, an ester, or a thioester, respectively. For example a glycopeptide compound of formula I wherein $R^3$ is a nitrogen linked moiety comprising one or more phosphono groups can be prepared by coupling a corresponding glycopeptide compound of formula I wherein $R^3$ is hydroxy with the requisite phosphono-containing amine to form the formula I wherein $R^3$ is a nitrogen linked moiety comprising one or more phosphono groups.

A glycopeptide compound which is substituted at the C-terminus with a substituent that comprises one or more (e.g. 1, 2, 3, 4, or 5) phosphono (—$PO_3H_2$) groups, and wherein the vancosamine amino terminus (V) is substituted, can be prepared by first reductively alkylating the corresponding glycopeptide compound wherein the vancosamine amino terminus (V) is the free amine ($NH_2$) and then coupling the corresponding glycopeptide compound with the requisite phosphono containing compound (e.g. phosphono containing amine, alcohol, or thiol).

By way of illustration, a glycopeptide compound, such as vancomycin, can first be reductive alkylated as shown in the following reaction:

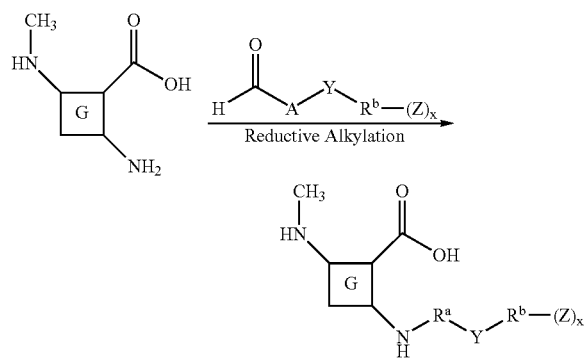

where A represents $R^a$ minus one carbon atom and $R^a$, $R^b$, Y, Z and x are as defined herein. This reaction is typically conducted by first contacting one equivalent of the glycopeptide, i.e., vancomycin, with an excess, preferably from 1.1 to 1.3 equivalents, of the desired aldehyde in the presence of an excess, preferably about 2.0 equivalents, of a tertiary amine, such as diisopropylethylamine (DIPEA) and the like. This reaction is typically conducted in an inert diluent, such as DMF or acetonitrile/water, at ambient temperature for about 0.25 to 2 hours until formation of the corresponding imine and/or hemiaminal is substantially complete. The resulting imine and/or hemiaminal is typically not isolated, but is reacted in situ with a reducing agent, such as sodium cyanoborohydride, pyridine borane, or the like, to afford the corresponding amine. This reaction is preferably conducted by contacting the imine and/or hemiaminal with an excess, preferably about 3 equivalents, of trifluoroacetic acid, followed by about 1 to 1.2 equivalents of the reducing agent at ambient temperature in methanol or acetonitrile/water. The resulting alkylated product is readily purified by conventional procedures, such as precipitation and/or reverse-phase HPLC. Surprisingly, by forming the imine and/or hemiaminal in the presence of a trialkyl amine, and then acidifying with trifluoroacetic acid before contact with the reducing agent, the selectivity for the reductive alkylating reaction is greatly improved, i.e., reductive alkylating at the amino group of the saccharide (e.g., vancosamine) is favored over reductive alkylating at the N-terminus (e.g., the leucinyl group) by at least 10:1, more preferably 20:1.

The above process is a significantly improvement over previous methods for selectively alkylating an amino saccharide group of a glycopeptide antibiotic. A method for alkylating a glycopeptide that comprises a saccharide-amine comprises:

combining an aldehyde or ketone, a suitable base, and the glycopeptide, to provide a reaction mixture;

acidifying the reaction mixture; and combining the reaction mixture with a suitable reducing agent, to provide a glycopeptide that is alkylated at the saccharide-amine. Preferably, the glycopeptide comprises at least one amino group other than the saccharide-amine.

Preferably, the reductive alkylating at the saccharide-amine is favored over reductive alkylating at another amino group of the glycopeptide by at least about 10:1; and more preferably, by at least about 15:1 or about 20:1.

The reductive alkylating process is typically carried out in the presence of a suitable solvent or combination of solvents, such as, for example, a halogenated hydrocarbon (e.g. methylene chloride), a linear or branched ether (e.g. diethyl ether, tetrahydrofuran), an aromatic hydrocarbon (e.g. benzene or toluene), an alcohol (methanol, ethanol, or isopropanol), dimethylsulfoxide (DMSO), N,N-dimethylformamide, acetonitrile, water, 1,3-dimethyl-3,4,5,6-tetrahydro-2(1H)-pyrimidone, tetramethyl urea, N,N-dimethylacetamide, diethylformamide (DMF), 1-methyl-2-pyrrolidinone, tetramethylenesulfoxide, glycerol, ethyl acetate, isopropyl acetate, N,N-dimethylpropylene urea (DMPU) or dioxane. Preferably the alkylating is carried out in acetonitrile/water, or DMF/methanol.

Preferably the reduction (i.e. treatment with the reducing agent) is carried out in the presence of a protic solvent, such as, for example, an alcohol (e.g. methanol, ethanol, propanol, isopropanol, or butanol), water, or the like.

The reductive alkylating process of the invention can be carried out at any suitable temperature from the freezing point to the reflux temperature of the reaction mixture. Preferably the reaction is carried out at a temperature in the range of about 0° C. to about 100° C. More preferably at a temperature in a range of about 0° C. to about 50° C., or in a range of about 20° C. to about 30° C.

Any suitable base can be employed in the reductive alkylating process of the invention. Suitable bases include tertiary amines (e.g. diisopropylethylamine, N-methylmorpholine or triethylamine) and the like.

Any suitable acid can be used to acidify the reaction mixture. Suitable acids include carboxylic acids (e.g. acetic acid, trichloroacetic acid, citric acid, formic acid, or trifluoroacetic acid), mineral acids (e.g. hydrochloric acid, sulfuric acid, or phosphoric acid), and the like. A preferred acid is trifluoroacetic acid.

Suitable reducing agents for carrying out reductive alkylating process of the invention are known in the art. Any suitable reducing agent can be employed in the methods of the invention, provided it is compatible with the functionality present in the glycopeptide. For example, suitable reducing agents include sodium cyanoborohydride, sodium triacetoxyborohydride, pyridine/borane, sodium borohydride, and zinc borohydride. The reduction can also be carried out in the presence of a transition metal catalyst (e.g. palladium or platinum) in the presence of a hydrogen source (e.g. hydrogen gas or cyclohexadiene). See for example, *Advanced Organic Chemistry*, Fourth Edition, John Wiley & Sons, New York (1992), 899-900.

The glycopeptide derivative resulting from the reductive alkylating is then coupled with a phosphono containing amine ($R^3$—H) to form an amide bond. This reaction is illustrated by the following reaction:

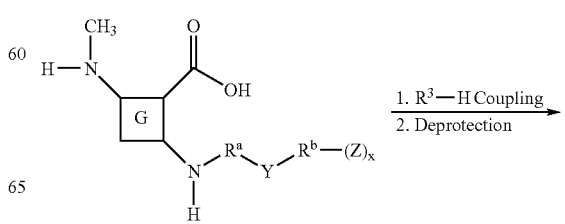

-continued

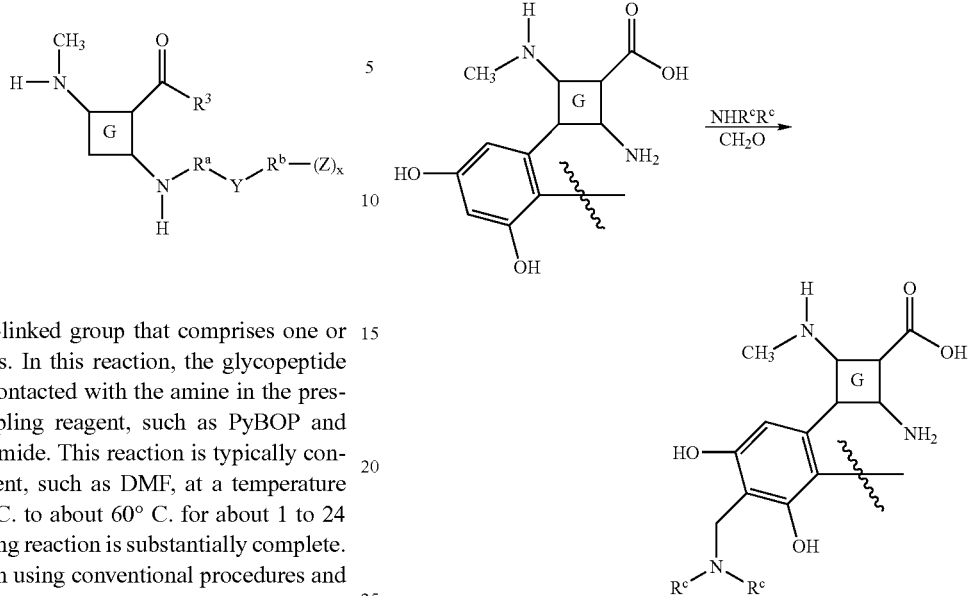

where R³ is a nitrogen-linked group that comprises one or more phosphono groups. In this reaction, the glycopeptide derivative is typically contacted with the amine in the presence of a peptide coupling reagent, such as PyBOP and HOBT, to provide the amide. This reaction is typically conducted in an inert diluent, such as DMF, at a temperature ranging from about 0° C. to about 60° C. for about 1 to 24 hours or until the coupling reaction is substantially complete. Subsequent deprotection using conventional procedures and reagents affords the compound of this invention.

If desired, the amine coupling step described above can be conducted first to provide an amide, followed by reductive alkylating and deprotection to afford the compound of the invention.

If desired, the glycopeptide compounds can also be prepared in a step-wise manner in which a precursor to the —R$^a$—Y—R$^b$-(Z)$_x$ group is first attached the glycopeptide by reductive alkylating, followed by subsequent elaboration of the attached precursor using conventional reagent and procedures to form the —R$^a$—Y—R$^b$-(Z)$_x$ group. Additionally, ketones may also be employed in the above-described reductive alkylating reactions to afford α-substituted amines.

Any glycopeptide having an amino group may be employed in these reductive alkylating reactions. Such glycopeptides are well-known in the art and are either commercially available or may be isolated using conventional procedures. Suitable glycopeptides are disclosed, by way of example, in U.S. Pat. Nos. 3,067,099; 3,338,786; 3,803,306; 3,928,571; 3,952,095; 4,029,769; 4,051,237; 4,064,233; 4,122,168; 4,239,751; 4,303,646; 4,322,343; 4,378,348; 4,497,802; 4,504,467; 4,542,018; 4,547,488; 4,548,925; 4,548,974; 4,552,701; 4,558,008; 4,639,433; 4,643,987; 4,661,470; 4,694,069; 4,698,327; 4,782,042; 4,914,187; 4,935,238; 4,946,941; 4,994,555; 4,996,148; 5,187,082; 5,192,742; 5,312,738; 5,451,570; 5,591,714; 5,721,208; 5,750,509; 5,840,684; and 5,843,889. Preferably, the glycopeptide employed in the above reaction is vancomycin.

As illustrated in the following scheme, a phosphono containing aminoalkyl sidechain at the resorcinol moiety of a glycopeptide, such as vancomycin, can be introduced via a Mannich reaction (in this scheme, the resorcinol moiety of the glycopeptide is illustrated for clarity). In this reaction, an amine of formula NHRR' (wherein one or both of R and R' is a group that comprises one or more phosphono groups), and an aldehyde (e.g. CH₂O), such as formalin (a source of formaldehyde), are reacted with the glycopeptide under basic conditions to give the glycopeptide derivative.

Compounds of the invention comprising a sulfoxide or sulfone can be prepared from the corresponding thio compounds using conventional reagents and procedures. Suitable reagents for oxidizing a thio compound to a sulfoxide include, by way of example, hydrogen peroxide, peracides such as 3-chloroperoxybenzoic acid (MCPBA), sodium periodate, sodium chlorite, sodium hypochlorite, calcium hypochlorite, tert-butyl hypochlorite and the like. Chiral oxidizing reagents, (optically active reagents) may also be employed to provide chiral sulfoxides. Such optically active reagents are well-known in the art and include, for example, the reagents described in Kagen et al., *Synlett.*, 1990, 643-650.

The aldehydes and ketones employed in the above reactive alkylating reactions are also well-known in the art and are either commercially available or can be prepared by conventional procedures using commercially available starting materials and conventional reagents (for example see March, *Advanced Organic Chemistry*, Fourth Edition, John Wiley & Sons, New York (1992), and references cited therein).

The phosphono substituted compounds (e.g. the phosphono substituted amines, alcohols, or thiols) are either commercially available or can be prepared by conventional procedures using commercially available starting materials and reagents. See for example, *Advanced Organic Chemistry*, Jerry March, 4th ed, 1992, John Wiley and Sons, New York, page 959; and Frank R. Hartley (ed.) *The Chemistry of Organophosphorous Compounds*, vol. 1-4, John Wiley and Sons, New York (1996). Aminomethylphosphonic acid is commercially available from Aldrich Chemical Company, Milwaukee, Wis.

Additional details and other methods for preparing the compounds of this invention are described in the Examples below.

Purification Methods

The present invention provides methods of purifying the phosphono derivatives of glycopeptides described above by resin chromatography using resins based on copolymers of polystyrene and divinyl benzene. Numerous examples of such resins, which are characterized by porous beads with a pore size of from about 30 Å to about 1000 Å, are provided commercially. For the present invention, a preferred pore size of the resin is from about 50 Å to about 1000 Å. An exemplary list of resins useful in methods of the present invention is given in Table II below, including manufacturer, pore diameter, and bead size.

TABLE II

Polystyrene - divinyl benzene resins

| Resin | Pore Diameter (Å) | Bead Size (um) | Manufacturer |
|---|---|---|---|
| Amberchrome CG-300m | 300 | 50-100 | TosoHaas |
| Amberchrome CG-300s | 300 | 20-50 | TosoHaas |
| Amberchrome CG-1000s | 1000 | 20-50 | TosoHaas |
| Amberchrome CG-71m | 250 | 50-100 | TosoHaas |
| Amberlite XAD-2010 | 280 | 200-800 | Rohm&Haas |
| Amberlite XAD 1600 | ~100 | 350-450 | Rohm&Haas |
| Amberlite XAD 16 | 100 | 200-800 | Rohm&Haas |
| Amberlite XAD 16HP | 100 | 200-800 | Rohm&Haas |
| CHP-20P | 260 | 37-75 | Mitsubishi |
| HP-20 | 260 | 200-600 | Mitsubishi |
| HP-20SS | 260 | 63-150 | Mitsubishi |
| SP-20SS | 260 | 63-75 | Mitsubishi |
| CHP55Y | 260 | 25-35 | Mitsubishi |
| Optipore L-323 | 100 | 200-800 | Dow |
| SD-2 | 50 | 200-800 | Dow |

In an exemplary purification method, a polystyrene resin, such as a resin listed in Table II, is prepared by wetting in excess water and washing with water, optionally acidified, and/or with an aqueous solution of a polar organic solvent, optionally acidified, and loaded onto a chromatographic column. The sample of glycopeptide to be purified is dissolved in acidified water containing a polar organic solvent. The pH of the sample solution is preferably between about 2 and 5. A small portion of the sample solution is removed and used as a standard for HPLC analysis.

The sample solution is loaded onto the column and eluted with a second acidified aqueous solution of a polar organic solvent, which is collected from the column in fractions. Preferably, the second acidified aqueous solution is at a concentration of about 10 mM acid and is proportionally in a ratio of from about 1:4 to about 1:15 polar organic solvent:water.

Each fraction is monitored for presence of sample by thin layer chromatography. When no further sample is observed in the eluate, an elutant solution that is higher in organic content is used to wash the remaining sample from the column. The column is regenerated by washing with acidified polar organic solvent and with acidified water.

Fractions containing sample are analyzed by HPLC for sample concentration and purity. The fractions containing a sample concentration that is higher than a desired threshold are pooled and the purified product is isolated from the eluate. As described in the examples, the purified product can be recovered from the eluate by lyophilizing the pooled fractions.

Alternatively, the purified product can be isolated from the eluate by precipitation and filtration. For example, an excess of a polar organic solvent, such as acetonitrile, can be added to the eluate producing a solid precipitate of the purified product, which is then filtered.

Optionally, a solution that is more concentrated in the purified product than the eluate can be formed from the eluate in a first step of the isolation process. The product is then isolated from the more concentrated solution. For example, a more concentrated solution can be formed by adding NaCl to the combined eluate fractions, loading the resulting solution onto a chromatographic column containing a polystyrene divinyl benzene resin, such as the resins described above, and eluting with a solution containing a higher concentration of polar organic solvent than the concentration of the organic solvent in the prior chromatographic step. Alternatively, a more concentrated solution can be formed in a batch process using a polystyrene divinyl benzene resin by adding the resin to the eluate at low temperatures such that the product is absorbed onto the resin; filtering the resin, and desorbing the glycopeptide from the resin with a room temperature aqueous polar organic solution.

As described in Example 4 below, using the present method, samples with an initial concentration of phosphonated glycopeptide that is between 67 and 74% have been purified to a concentration that is between about 83 and 94%.

While the purification method has been described using column chromatography, as known in the art the sample solution may be contacted with the resin in alternative arrangements, such as using a batch processing vessel.

The following examples are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius.

ACN=acetonitrile
BOC, Boc=tert-butoxycarbonyl
DIBAL-H=diisobutylaluminum hydride
DIPEA=diisopropylethylamine
DMF=N,N-dimethylformamide
DMSO=dimethyl sulfoxide
eq.=equivalent
EtOAc=ethyl acetate
Fmoc=9-fluorenylmethoxycarbonyl
HOBT=1-hydroxybenzotriazole hydrate
Me=methyl
MS=mass spectroscopy
PyBOP=benzotriazol-1-yloxytris(pyrrolidino)phosphonium hexafluorophosphate
TEMPO=2,2,6,6-tetramethyl-piperidinyloxy, free radical
TFA=trifluoroacetic acid
THF=tetrahydrofuran
TLC, tlc=thin layer chromatography In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

General Procedure A

Reductive Alkylating of Vancomycin

To a mixture of vancomycin (1 eq.) and the desired aldehyde (1.3 eq.) in DMF was added DIPEA (2 eq.). The reaction was stirred at ambient temperature for 1-2 hours and monitored by reverse-phase HPLC. Methanol and NaCNBH$_3$ (1 eq.) were added to the solution, followed by TFA (3 eq.). Stirring was continued for an additional hour at ambient temperature. After the reaction was complete, the methanol was removed in vacuo. The residue was precipitated in acetonitrile. Filtration gave the crude product which was then purified by reverse-phase HPLC. If desired, other glycopeptides antibiotics may be used in this procedure.

General Procedure B

Synthesis of 2-(Decylthio)acetaldehyde

Under nitrogen, to a suspension of potassium carbonate (27 g, 200 mmol) in acetone (100 ml) was added decyl bromide (10 ml, 50 mmol) and mercaptoethanol (4.4 ml, 63 mmol). The suspension was stirred at room temperature for 2 days, then partitioned between water and 80% hexane/ethyl acetate. The organic phase was washed with 2N sodium hydroxide, dried over magnesium sulfate, and the volatiles removed under vacuum to give 2-(decylthio)ethanol (10.2 g, 47 mmol) as a colorless liquid that was used without further purification.

Under nitrogen, 2-(decylthio)ethanol (50 g, 230 mmol), N,N-diisopropylethylamine (128 ml, 730 mmol) and methylene chloride (400 ml) were cooled to −40° C. To this solution was added, over 15 minutes, a solution of sulfur trioxide pyridine complex (116 g, 730 mmol) in dimethyl sulfoxide (600 ml) and methylene chloride (200 ml). After addition, the mixture was stirred a further 15 minutes at −40° C., then 600 ml ice water as added. The mixture was removed from the cooling bath, 1 L water was added, and the liquids partitioned. The organic phase was washed with 1 L of 1 N hydrochloric acid, and dried over magnesium sulfate. Filtration gave 600 ml liquid, which was diluted with 600 ml hexane and passed through 200 ml silica. The silica was washed with 100 ml 50% methylene chloride/hexane, then 300 ml methylene chloride. The combined organics were concentrated in vacuo to give 2-(decylthio)acetaldehyde (48 g, 220 mmol) as a colorless liquid that was used without further purification.

General Procedure C

Synthesis of $N^{van}$-2-(Decylthio)ethyl Vancomycin

Procedure A: Under nitrogen, vancomycin hydrochloride hydrate (1 g, 0.64 mmol) was added to 2-(decylthio)acetaldehyde (139 mg, 0.64 mmol) in N,N-dimethylformamide (8 ml). N,N-diisopropylethylamine (336 uL, 1.9 mmol) was added and the suspension stirred vigorously for 2.5 hours, over the course of which all the vancomycin dissolved. Solid sodium cyanoborohydride (60 mg, 0.96 mmol) was added, followed by methanol (5 ml) and trifluoroacetic acid (250 uL, 3.2 mmol). The reaction was stirred for 55 minutes at room temperature and analyzed by reverse phase HPLC. The product distribution based on uv absorption at 280 nm was as follows:

| Elution time (min) | Area % | Product |
| --- | --- | --- |
| 2.0 | 29 | vancomycin |
| 3.1 | 50 | $N^{van}$-2-(decylthio)ethyl vancomycin |
| 3.2 | 2 | — |
| 3.3 | 7 | $N^{leu}$-2-(decylthio)ethyl vancomycin |
| 3.9 | 13 | $N^{van},N^{leu}$-bis-[2-(decylthio)ethyl] vancomycin |
| 4.0 | 0.5 | — |

Procedure B: Under nitrogen, to a solution of 2-(decylthio)acetaldehyde (crude, 48 g, 220 mmol) in N,N-dimethylformamide (1.4 L) was added solid vancomycin hydrochloride hydrate (173 g, 110 mmol) followed by N,N-diisopropylethylamine (58 ml, 330 mmol). The suspension was stirred vigorously at room temperature for 2 hours, in the course of which time all the vancomycin fully dissolved, then trifluoroacetic acid (53 ml, 690 mmol) was added. The solution was stirred a further 90 minutes, then solid sodium cyanoborohydride (10.5 g, 170 mmol) followed by methanol (800 ml) were added. After three hours the reaction was analyzed by reverse-phase HPLC. The product distribution based on uv absorption at 280 nm was as follows:

| Elution time (min) | Area % | Product |
| --- | --- | --- |
| 2.0 | 15 | vancomycin |
| 3.2 | 77 | $N^{van}$-2-(decylthio)ethyl vancomycin |
| 3.3 | 3 | — |
| 3.4 | 0.5 | $N^{leu}$-2-(decylthio)ethyl vancomycin |
| 4.0 | 0.8 | $N^{van},N^{leu}$-bis-[2-(decylthio)ethyl] vancomycin |
| 4.1 | 4 | — |

The reaction mixture from either of the above procedures was poured into water (7 L), resulting in a slightly cloudy solution. The pH of the solution was adjusted to 5 with saturated sodium bicarbonate, resulting in the formation of a white precipitate. This precipitate was collected by filtration, washed with water then ethyl acetate and dried under vacuum to afford $N^{van}$-2-(decylthio)ethyl vancomycin, which was used without further purification.

Procedure C: A solution of vancomycin hydrochloride (3.0 g, 2.1 mmol) in ACN/H$_2$O (1:1, 30 ml) was treated with diisopropylethylamine (0.54 g, 0.72 ml, 4.2 mmol) followed by 2-(decylthio)acetaldehyde (0.91 g, 4.2 mmol) at 25° C. After 30 min, the reaction mixture was treated with TFA (1.92 g, 1.29 ml, 16.8 mmol) followed by NaCNBH$_3$ (0.132 g, 2.1 mmol). After 5 to 10 minutes, the crude product $N^{van}$-2-(decylthio)ethyl vancomycin is precipitated in acetonitrile (300 ml).

Example 1

Preparation of Compound 3

Formula I wherein $R^3$ is N-(phosphonomethyl)-amino; $R^5$ is hydrogen; $R^{19}$ is hydrogen, and $R^{20}$ is —CH$_2$CH$_2$—S—(CH$_2$)$_9$CH$_3$ $N^{VAN}$-(2-decylthio)ethyl vancomycin bistrifluoroacetate (1 g, 0.53 mmol) and diisopropylethylamine (0.23 ml, 1.33 mmol) were combined in DMF (10 ml) and stirred until homogeneous. HOBt (0.080 g, 0.58 mmol) and PYBOP (0.300 g, 0.58 mmol) were then added to the reaction mixture. After 5-10 minutes a homogeneous solution containing (aminomethyl)phosphonic acid (0.060 g, 0.53 mmol) and diisopropylethylamine (0.23 ml, 1.33 mmol) in water (3 ml) was added. The reaction was stirred at room temperature and monitored by MS. When the reaction was judged to be complete, the reaction mixture was diluted with acetonitrile (40 ml) and centrifuged. The supernatant was discarded and the remaining pellet containing desired product was dissolved in 50% aqueous acetonitrile (10 ml) and purified by reverse phase preparative HPLC to give the title compound. MS calculated (M+) 1742.7. Found (MH+) 1743.6.

Example 2

Preparation of Compound 11

(Formula I wherein $R^3$ is —OH; $R^5$N-(phosphonomethyl)-aminomethyl; $R^{19}$ is hydrogen, and $R^{20}$ is —CH$_2$CH$_2$—NH—(CH$_2$)$_9$CH$_3$)

(Aminomethyl)phosphonic acid (3.88 g, 35 mmol) and diisopropylethylamine (6.1 ml, 35 mmol) were combined in water (40 ml) and stirred until homogeneous. Acetonitrile (50 ml) and formaldehyde (37% solution in $H_2O$; 0.42 ml, 05.6 mmol) were then added to the reaction mixture. After approximately 15 minutes both $N^{VAN}$-decylaminoethyl vancomycin tristrifluoroacetate (10.0 g, 5.1 mmol) and diisopropylethylamine (6.1 ml, 35 mmol) were added to the reaction mixture. The reaction was stirred at room temperature for approximately 18 hrs, at which time the pH was adjusted to about 7 with 20% TFA, acetonitrile was removed in vacuo, and the residue was lyophilized. The resulting solid was triturated with water (100 mL), collected by filtration, dried in vacuo and purified by reverse phase preparative HPLC to give the title compound. MS calculated (MH+) 1756.6. Found (MH+) 1756.6.

Compound 11 was also prepared as follows.

The quinuclidine salt of $N^{VAN}$-(decylaminoethyl)vancomycin (500 mg, 0.28 mmol, sub-part f below) and aminomethylphosphonic acid (155 mg, 1.4 mmol) were slurried in 50% aqueous acetonitrile (10 mL). Diisopropyl-ethylamine (972 uL, 720 mg, 5.6 mmol) was added and the mixture stirred at room temperature until the solids had dissolved. The reaction mixture was then cooled in an ice bath and formalin (3.7%, made by diluting commercial 37% formalin 1:9 with 50% ACN/water, 220 uL, 8.8 mg, 0.29 mmol) was added. The reaction mixture was stirred at 0° for 15 hours, at which time the reaction to be complete. The reaction was quenched at 0° by adding 3N HCl to about pH 2. The mixture was diluted to 50 mL with 50% ACN/water, and then acetonitrile was added (75 mL, followed by 5×10 mL at 5 minute intervals, 125 mL total) to precipitate the product. The solid was collected by vacuum filtration and dried in vacuo. Purification by reverse phase preparative HPLC gave the title compound.

The intermediate $N^{VAN}$-decylaminoethyl vancomycin tristrifluoroacetate was prepared as follows.

a. N-Fmoc-2-(decylamino)ethanol. 2-(n-Decylamino)ethanol (2.3 g, 11 mmol, 1.1 eq) and DIPEA (2.0 ml, 11 mmol, 1.1 eq) were dissolved in methylene chloride (15 ml) and cooled in an ice bath. 9-Fluorenylmethyl chloroformate (2.6 g, 10 mmol, 1.0 eq) in methylene chloride (15 ml) was added, the mixture stirred for 30 minutes then washed with 3N hydrochloric acid (50 ml) twice and saturated sodium bicarbonate (50 ml). The organics were dried over magnesium sulfate, and the solvents removed under reduced pressure. N-Fmoc-2-(decylamino)ethanol (4.6 g, 11 mmol, 108%) was used without further purification.

b. N-Fmoc-decylaminoacetaldehyde. To a solution of oxalyl chloride (12.24 ml) and methylene chloride (50 mL) at −35 to −45° C. was added DMSO (14.75 g) in methylene chloride (25 mL) over 20 minutes. The reaction mixture was stirred for 10 minutes at −35 to −45° C. A solution of N-Fmoc-decylaminoethanol (20.0 g) in methylene chloride (70 mL) was added over 25 minutes and then stirred 40 minutes at −35 to −45° C. Triethylamine (21.49 g) was then added and the mixture stirred for 30 minutes at −10 to −20° C. The reaction mixture was quenched with water (120 mL) followed by concentrated sulfuric acid (20.0 g) while maintaining the internal temperature at 0-5° C. The organic layer was isolated and washed with 2% sulfuric acid (100 mL) followed by water (2×100 mL). The organic solution was distilled under vacuum at 60° C. to about 100 mL. Heptane (100 mL) was added, the temperature of the oil bath raised to 80° C. and the distillation was continued until the residual volume was 100 mL. More heptane (100 mL) was added and the distillation repeated to a volume of 100 mL. The heating bath was replaced with a cold water bath at 15° C. The bath was cooled slowly to 5° C. over 20 minutes to start the precipitation of the product. The slurry was then cooled to −5 to −10° C. and the slurry was stirred for 2 hours. The solid was then collected on a Buchner funnel and washed with cold (−5° C.) heptane (2×15 mL). The wet solid was dried in vacuo to yield the aldehyde.

c. $N^{van}$—(N-Fmoc-2-n-decylaminoethyl) vancomycin trifluoroacetate. Vancomycin hydrochloride (12 g, 7.7 mmol, 1.0 eq), N-Fmoc-2-(n-decylamino)-acetaldehyde (3.2 g, 7.6 mmol, 1.0 eq) and DIPEA (2.6 ml, 14.9 mmol, 2.0 eq) were stirred at room temperature in DMF (120 ml) for 90 minutes. Sodium cyanoborohydride (1.4 g, 22 mmol, 3.0 eq) was added, followed by methanol (120 ml) then trifluoroacetic acid (1.8 ml, 23 mmol, 3.0 eq). The mixture was stirred for 60 minutes at room temperature, then the methanol removed under reduced pressure. The resulting solution was added to 600 ml diethyl ether giving a precipitate which was filtered, washed with ether, and dried under vacuum. The crude product was purified on a reverse-phase flash column, eluting with 10, 20, 30% acetonitrile in water (containing 0.1% trifluoroacetic acid) to remove polar impurities (such as residual vancomycin) then the product was eluted with 70% acetonitrile in water (containing 0.1% trifluoroacetic acid) to give 9 g of $N^{van}$—(N-Fmoc-2-n-decylaminoethyl) vancomycin as its trifluoroacetate salt (4.3 mmol, 56%).

d. $N^{van}$-2-(n-Decylamino)ethyl vancomycin trifluoroacetate. $N^{van}$—(N-Fmoc-2-n-decylaminoethyl) vancomycin (100 mg) was dissolved in 1 ml DMF (1 ml) and treated with piperidine (200 uL) for 30 minutes. The mixture was precipitated into ether, centrifuged and washed with acetonitrile. Reverse-phase preparative HPLC (10-70% acetonitrile in water containing 0.1% trifluoroacetic acid over 120 minutes) gave $N^{van}$-2-(n-decylamino)ethyl vancomycin as its TFA salt.

The intermediate quinuclidine salt of $N^{VAN}$-decylaminoethyl vancomycin was prepared as follows.

e. N"-(N'-Fmoc-decylaminoethyl) vancomycin. To a 2 L flask equipped with a mechanical stirrer was added vancomycin hydrochloride (50.0 g), N-Fmoc-decylaminoacetaldehyde (13.5 g), DMF (400 mL) and N,N-diisopropylethylamine (11.7 mL). The suspension was stirred at room temperature for 2 hours, at which time the solids had dissolved. Methanol (190 mL) followed by trifluoroacetic acid (10.4 mL) was added. After the reaction mixture had stirred for 5 minutes, borane-pyridine complex (3.33 g) was added in one portion, and rinsed in with methanol (10 mL). After stirring 4 hours, the reaction was cooled to 5-10° C. with an ice bath and water (675 mL) was added at a rate to keep the temperature below 20° C. The reaction mixture was warmed to room temperature and 10% NaOH was added to pH 4.2-4.3 (approx 15 mL). The resultant slurry was cooled in an ice bath for 1 hour, and then the product is collected by vacuum filtration and washed with cold water (2×100 mL). The wet solid was dried in vacuo at 50° C. to give the title compound as an off-white to pale-pink solid.

f. $N^{VAN}$-(decylaminoethyl) vancomycin quinuclidine salt. $N^{van}$—(N'-Fmoc-decylaminoethyl) vancomycin (88 g, 42 mmol) was dissolved in DMF (500 mL) by stirring at room temperature for 1 hour. Quinuclidine (9.4 g, 84 mmol) was added, and the reaction mixture stirred for 18 hours. The DMF was removed in vacuo and the solid was triturated with acetonitrile (700 mL) for 3 hours. The solid was collected on a Buchner funnel and triturated with acetonitrile (200 mL) for 16 hours. More acetonitrile (700 mL) was added at this time, and the solid was collected on a Buchner funnel, washed with acetonitrile (500 mL), and then resuspended in acetonitrile (500 mL). After stirring for 2 hours, the solid was collected on a Buchner funnel and dried in vacuo to give the title compound.

Example 3

Preparation of Compound 12

(Formula I wherein $R^3$ is —OH; $R^5$N-(phosphonomethyl)-aminomethyl; $R^{19}$ is hydrogen, and $R^{20}$ is —$CH_2CH_2$—S—$(CH_2)_9CH_3$)

(Aminomethyl)phosphonic acid (0.295 g, 266 mmol) and diisopropylethylamine (0.649 ml, 3.72 mmol) were combined in water (5 ml) and stirred until homogeneous. Formaldehyde (37% solution in $H_2O$; 0.044 ml, 0.585 mmol) and acetonitrile (5 ml) were then added to the reaction mixture. After approximately 15 minutes both $N^{VAN}$-(2-decylthio)ethyl vancomycin bistrifluoroacetate (1 g, 0.53 mmol) and diisopropylethylamine (0.649 ml, 3.72 mmol) were added to the reaction mixture. The reaction was stirred at room temperature for approximately 18 hrs, at which time the reaction mixture was diluted with ACN (40 ml) and centrifuged. The supernatant was discarded and the remaining pellet containing desired product was dissolved in 50% aqueous acetonitrile (10 ml) and purified by reverse phase preparative HPLC to give the title compound. MS calculated (M+) 1772.7. Found (MH+) 1773.4.

Using the above procedures and the appropriate starting materials the compounds shown in Table I were prepared. The mass spectral data for these compounds were as follows:

| Compound No. | MW (freebase) | Observed MH+ |
| --- | --- | --- |
| 1 | 1725.63 | 1726.6 |
| 2 | 1726.62 | 1727.5 |
| 3 | 1742.68 | 1743.6 |
| 4 | 1724.64 | 1725.6 |
| 5 | 1742.96 | 1743.6 |
| 6 | 1786.03 | 1786.4 |
| 7 | 1785.04 | 1785.8 |
| 8 | 1799.07 | 1799.7 |
| 9 | 1770.74 | 1771.8 |
| 10 | 1772.99 | 1774.3 |
| 11 | 1755.66 | 1756.6 |
| 12 | 1772.71 | 1773.4 |
| 13 | 1756.64 | 1757.6 |
| 14 | 1754.67 | 1755.7 |
| 15 | 1772.99 | 1773.7 |
| 16 | 1816.06 | 1816.5 |
| 17 | 1815.01 | 1816.2 |
| 18 | 1829.10 | 1829.8 |
| 19 | 1878.1 | 1878.2 |
| 20 | 1802.74 | 1803.5 |
| 21 | 1830.75 | 1831.7 |
| 22 | 1849.66 | 1850.6 |
| 23 | 1800.76 | 1801.6 |
| 24 | 1801.04 | 1801.6 |
| 25 | 1932.86 | 1934.0 |
| 26 | 1880.12 | 1880.7 |

Example 4

Purification of Compound 11

(Formula I wherein $R^3$ is —OH; $R^5$N-(phosphonomethyl)-aminomethyl; $R^{19}$ is hydrogen, and $R^{20}$ is —$CH_2CH_2$—NH—$(CH_2)_9CH_3$)

2 g of Amberlite XAD 1600 was combined with an excess of HPLC grade water for 4 hours. The excess water was removed, and the resin was washed successively with (1) excess HPLC grade water; (2) excess 10 mM Acetic Acid in methanol; (3) excess 10 mM acetic acid in 50/50 v/v ACN/water; (4) excess 5/95 v/v acetic acid/water; and (5) excess 10/90 v/v acetic acid/water.

The resin was loaded onto a 1 cm internal diameter column (Omnifit #56001) fitted with a 20 psi back pressure regulator (Upchurch P-791), a peristaltic pump (Ranin Dynamax Model RP-1) and a fraction collector (BioRad 2110), adjusted to provide a flow rate of elutant solution of 1 bed volume per hour, yielding 1 ml fractions.

The sample was prepared by dissolving 50 mg of crude compound 11 in 5 ml of 10/90 v/v acetic acid/water. The solution was sonicated for 5 minutes, and loaded onto the column at the 1 bed volume/hour flow rate. Twenty microliters of the loading solution was diluted 1:50 v/v with water and used as a standard for HPLC analysis.

The loaded sample was eluted with 10 mM acetic acid in 17.5/82.5 v/v ACN/water. Each fraction was collected and tested for the presence of sample by thin layer chromatography (TLC). Each fraction was spotted onto the TLC plate (EM Science #15341) and compared to reference spots from the loading solution to confirm the presence of compound 11. Fractions were collected until compound 11 was no longer detected by TLC. The elutant solution was then switched to 10 mm acetic acid in 50/50 v/v ACN/water in order to wash off any remaining sample still on the column. The wash-off fractions were also tested by TLC for the presence of sample. Once the sample was no longer seen in the wash off, fraction collection was ended. The column was then washed in 5 bed volumes each of 10 mM acetic acid in methanol, 10 mM acetic acid in 50/50 v/v ACN/water, and 10/90 v/v acetic acid/water.

Each fraction was vortexed, and diluted 1:10 with water into auto sampler vials. The auto sampler vials were vortexed and analyzed on a Varian HPLC system with ultraviolet detection at 214 nm. 20 microliters of each diluted fraction was injected onto a room temperature Zorbax Bonus-RP, 4.6×150 mm column. The sample was eluted off the column with a 7 minute gradient from 82% A (5/95 v/v ACN/water 0.1% TFA) 18% B (95/5 ACN/water, 0.1% TFA) to 60% A/40% B.

Fractions that contained more than 89% pure compound 11 were pooled. The pooled fractions were lyophilized overnight on a VirTis benchtop lyophilizer, and weighed to determine yield. The solid compound 11 was dissolved in 10/90 v/v acetic acid/water and diluted to 100 micrograms/milliliter in water. The 100 microgram/ml pure compound 11 was analyzed with the above HPLC method to verify its purity. The corrected yield is determined from the following formula:

% yield compound 11=[(mg purified)(% compound 11 in purified)]/[(mg crude loaded)(% compound 11 in crude)]×100%

As shown below in the first line of Table III, the starting concentration of 74% compound 11 was purified to a concentration of 90% at a 59% yield.

Examples 5-13

Purification of Compound 11 with Multiple Resins and Elutant Solutions

Compound 11 was purified by the process of Example 4 using a variety of resins and elutant solutions. Results are listed below in Table III.

TABLE III

Purification of Compound 11

| Ex | Resin | Elutant Phase | Initial % | Final % | % Yield |
|---|---|---|---|---|---|
| 4 | Amberlite XAD 1600 | 17.5/82.5 ACN/Water, 10 mM Acetic Acid | 74 | 90 | 59 |
| 5 | Amberlite XAD 16 | 17.5/82.5 ACN/Water, 10 mM Acetic Acid | 74 | 84 | 69 |
| 6 | Amberchrome CG-300S | 12/88 IPA/Water, 2 mM HCl | 67 | 86 | 78 |
| 7 | Diaion HP 20 | 17.5/82.5 ACN/Water, 10 mM Acetic Acid | 74 | 85 | 39 |
| 8 | Amberlite XAD 16HP | 17.5/82.5 ACN/Water, 10 mM Acetic Acid | 74 | 87 | 27 |
| 9 | Amberlite XAD 1600 | 17.5/82.5 ACN/Water, 2 mM HCl | 74 | 85 | 48 |
| 10 | Amberlite XAD 1600 | 17.5/82.5 ACN/Water, 0.05% TFA | 74 | 94 | 36 |
| 11 | Optipore SD-2 | 17.5/82.5 ACN/Water, 10 mM Acetic Acid | 74 | 83 | 70 |
| 12 | Amberchrome CG1000s | 12/88 IPA/Water, 2 mM HCl | 70 | 90 | 42 |
| 13 | CHP-20P | 12/88 ACN/Water, 2 mM HCl | 68 | 83 | 11 |

From the above results, it is apparent that methods of the present invention provide purification of phosphonated glycopeptide derivatives to purities in excess of 80%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A process for purifying a compound of the formula:

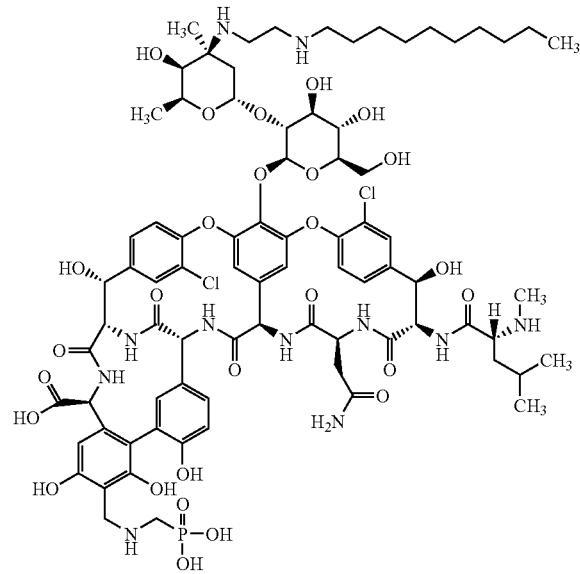

or a salt thereof; the process comprising eluting the compound or a salt thereof from a polystyrene divinyl benzene resin using an acidified aqueous solution containing a polar organic solvent.

2. The method of claim 1, wherein the polystyrene divinyl benzene resin has a pore size of from about 50 Å to about 1000 Å.

3. The method of claim 1, wherein the polystyrene divinyl benzene resin has a particle bead size in the range of between about 20 μm to about 800 μm.

4. The method of claim 1, wherein the polar organic solvent is ethanol.

5. The method of claim 1, wherein the polar organic solvent is acetonitrile.

6. The method of claim 1, wherein the acidified aqueous solution contains acetic acid.

7. The method of claim 1, wherein the acidified aqueous solution contains hydrochloric acid.

* * * * *